United States Patent [19]

Oscarsson

[11] Patent Number: 4,645,496
[45] Date of Patent: Feb. 24, 1987

[54] CONTINUOUS CATHETER FLUSHING FLOW CONTROL DEVICE

[75] Inventor: Rolf A. Oscarsson, Hudson, Ohio

[73] Assignee: RAO Medical Devices, Inc., Hudson, Ohio

[21] Appl. No.: 817,416

[22] Filed: Jan. 9, 1986

[51] Int. Cl.⁴ .................. A61M 5/00; A61B 5/02
[52] U.S. Cl. .................. 604/248; 128/673; 251/117
[58] Field of Search .......... 128/673, 675, 685; 604/118, 246, 248, 30, 257, 266, 267; 251/117, 209, 118, 309; 137/238

[56] References Cited

U.S. PATENT DOCUMENTS

| | | | |
|---|---|---|---|
| 3,675,891 | 7/1972 | Reynolds | 251/117 |
| 3,812,882 | 5/1974 | Taylor | 251/304 X |
| 3,877,428 | 4/1975 | Seagle et al. | 604/248 |
| 4,177,947 | 12/1979 | Menzel | 251/209 X |
| 4,192,303 | 3/1980 | Young et al. | 251/117 |
| 4,200,119 | 4/1980 | Cunningham | 251/117 |
| 4,245,636 | 1/1981 | Sparks | 251/117 |
| 4,267,835 | 5/1981 | Barger et al. | 251/342 |
| 4,278,083 | 7/1981 | Young et al. | 251/117 |
| 4,497,468 | 2/1985 | Hubbard et al. | 251/117 |
| 4,509,946 | 4/1985 | McFarlane | 604/246 |
| 4,550,748 | 11/1985 | Nunez | 251/117 |

*Primary Examiner*—Stephen C. Pellegrino
*Attorney, Agent, or Firm*—Body, Vickers & Daniels

[57] ABSTRACT

A flow regulating valve device providing continuous flushing of intravascular catheters with a flushing solution at either a restricted normal slow flow rate or intermittently at a catheter flush-out fast flow rate. The valve device has a cylindrical drum element rotatably mounted within a cylindrical chamber of a body member and provided with a diametrical flow-restricting capillary passage and a circumferentially extending, arcuate groove fast flow bypass passageway which are selectively moved into respective flow controlling positions by rotative adjustment of the drum element within the chamber. Biasing spring means on the device normally bias and maintain the body and stem members in their restricted flow rate relative rotative position while actuating arm means on these members enable manual rotative displacement thereof to their fast flow relative rotative position.

31 Claims, 7 Drawing Figures

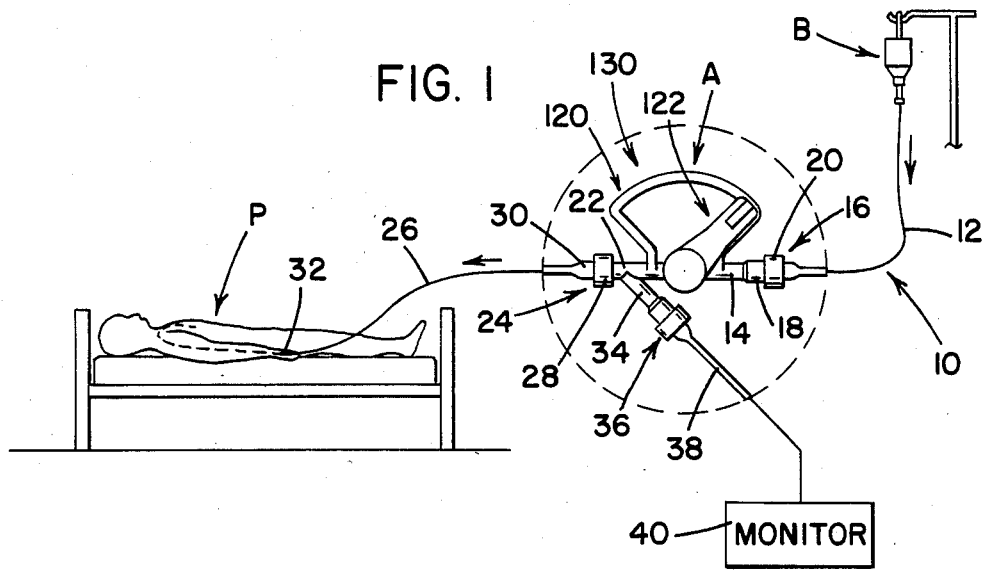
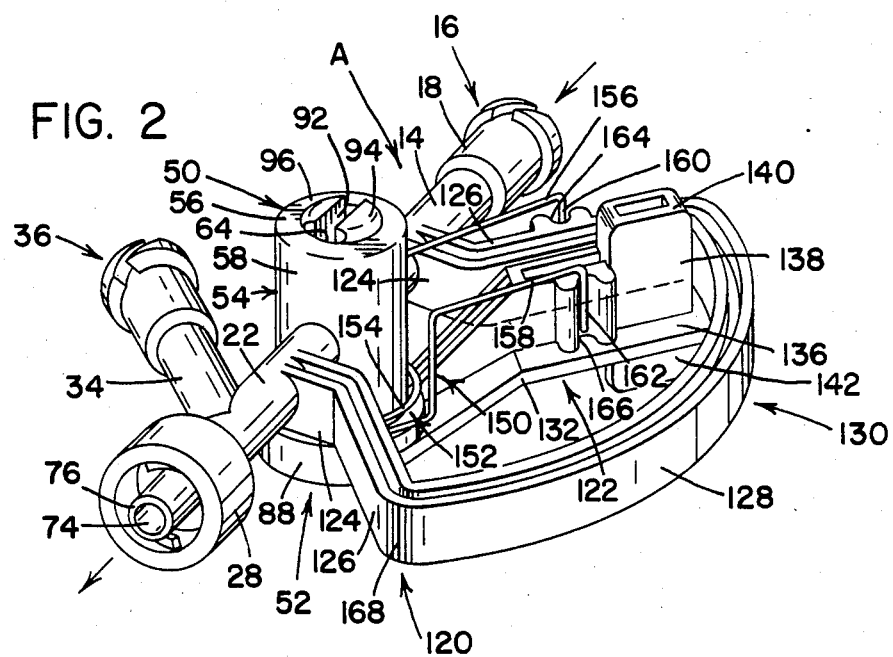

CONTINUOUS CATHETER FLUSHING FLOW CONTROL DEVICE

This invention relates in general to a flow control device for intravenous catheter systems used in monitoring arterial functions of, and infusion of medical fluids into a patient. More particularly, the invention relates to a flow control device for controlling the flow of the fluid at a desired continuous minute flow rate while permitting intermittent, manually controlled, larger flows of the fluid to rapidly flush the catheter system.

BACKGROUND OF THE INVENTION

It is common practice in the medical field to employ intravascular catheter systems for clinical monitoring and recording of a patient's arterial pulse waveforms to determine various parameters such as heart rate, stroke volume, cardiac output, duration of systole, and systolic, diastolic, and mean blood pressures. In addition, blood samples for intermittent arterial blood gas analysis purposes may be withdrawn from time to time from the patient by such catheter systems.

The catheter systems in general use at present ordinarily include a conventional catheter for injection into the patient's artery or vein and connected, through a tubing system containing a flow control device, to a source of parenteral liquid such as normal saline solution under pressure. The catheter is also connected, downstream of the flow control device, by a connecting tube to a pressure transducer for converting the physical blood pressure signals into an electrical impulse which is then fed to a recording machine such as an oscilloscope. The aforementioned connecting tube may be provided with a coupling for attachment thereto of a syringe for withdrawing blood samples from the patient from time to time for blood gas analysis.

In order to assure high fidelity clinical monitoring or recording of central arterial pulse waveforms by the use of such intravascular catheter systems, it has been necessary to continuously flush the inserted catheter, during use, with a regulated continuous infusion thereinto of a relatively small flow, e.g., around 3 cc to 7 cc per hour, of a parenteral liquid such as a normal saline solution, in order to prevent occlusion of the intravascular end of the catheter by blood coagulation. Catheter patency is thereby maintained for continuous monitoring or recording of the arterial pulse waveforms over periods of time which may amount to several days. The small amounts of parenteral liquid infused into the patient as a result of such continuous catheter flushing is easily absorbed by the patient's body and is in no way harmful. Continuous catheter flushing systems such as described and utilizing so-called marine-bore capillary tubes as flow resistors and applying the flushing solution under pressure have been employed heretofore, one such system being described in an article appearing on pages 675-678 of the Journal of Thoracic and Cardiovascular Surgery, Volume 57, No. 5, May 1969.

Prior to the insertion of an intravascular catheter such as described above into a patient's artery or vein for clinical monitoring of pulse waveforms, as well as periodically during the progress of such monitoring, it becomes necessary to flush a larger amount of the flushing solution through the catheter in order to prime or quickly fill the catheter tubing system with such solution in the first instance and eliminate any possible air bubbles therefrom, and particularly to ensure that the catheter is and remains completely free of coagulated blood. Various types of continuous catheter flushing systems for selectively providing either a slow or a fast flow rate of the flushing solution have been proposed heretofore. Thus, in U.S. Pat. No. 3,581,733, a saline flushing solution is directed by a stopcock either through a large capillary tube or through a larger separate bypass tube to a channel tubing connected to the catheter, and a second stopcock is connected between the catheter and the channel tubing to enable the quick and complete filling or priming of the tubing system with the flushing solution. Such a system is complicated to set-up, requiring several connections to stopcocks and tubing sections. Moreover, the use of stopcocks in the system results in a decrease of pressure pulse fidelity because of the often present minute leaks in the stopcocks.

Many of the above referred to deficiencies inherent in the earlier continuous catheter flushing system such as described above are overcome by the systems disclosed in U.S. Pat. Nos. 3,675,891 and 4,200,119 wherein a unitary flow control device connected in the tubing system supplying the flushing solution to the catheter is so constructed as to eliminate the use of all stopcocks and itself selectively provide either a capillary restricted flow rate or a fast flushing flow rate of the flushing solution to the catheter. In these improved catheter flushing systems, a spring biased valve is employed in the flow control device to control a bypass passageway in the device around the capillary flow resistor passageway therein, with the valve being manually operated either by pulling out or pushing in a valve stem, or a valve operating plunger, protruding from the device. Besides their being constituted of many component parts and involving complicated assembly procedures such as renders the device relatively expensive, these valve controlled devices also have certain other deficiencies such as possible accidental undesired opening of the valve or breakage of the valve stem so as to preclude proper operation of the device. Moreover, because of the yieldability of the resilient valves of these devices, the blood pressure pulses to which the valves are exposed during use are dampened at least to some degree by the yielding of the valve so that inaccuracies and loss of fidelity in the recorded pressure pulses will result. In this regard, the extremely sensitive pressure monitoring equipment ordinarily employed with continuous catheter flushing devices will sense and reflect any dampening of the pressure pulses caused by the continuous catheter flushing device.

More recently, as disclosed in U.S. Pat. Nos. 4,192,303: 4,245,636: 4,267,835: and, 4,278,083, improved continuous catheter flushing devices have been developed which, among other things, are of more simplified and less expensive construction and which employ a capillary flow resistor inner tube through which the flushing solution normally passes at a controlled slow rate, and a rubber-like outer sleeve spaced from but elastically gripping, at a region intermediate its ends, around the capillary inner tube to normally seal off the passageway between the capillary tube and the surrounding rubber sleeve. Squeezing of the rubber outer tube adjacent the seal then distorts it out of round so as to break the seal between the capillary tube and the surrounding rubber sleeve, thereby opening the passageway therebetween to form a bypass passageway for fast flow of the flushing solution through the device.

On removal of the squeezing force from the rubber sleeve, the latter then contracts to again grip around the capillary inner tube so as to restore the seal therebetween, thereby blocking the bypass passageway to then confine the flow of the flushing solution solely through the capillary tube. However, even with these improved continuous catheter flushing devices employing rubber outer sleeves distortable by squeezing to open a bypass passageway around the capillary inner tube, inaccuracies in the recorded blood pressure pulses have persisted. One reason for these inaccuracies is that the extremely sensitive blood pressure monitoring equipment normally employed at present with intravascular catheter systems will sense and reflect any dampening of the pressure pulses caused by the continuous catheter flushing device, thereby resulting in loss of fidelity in the recorded pressure pulse waveforms. As in the case of continuous catheter flushing systems as previously referred to and employing spring loaded valves normally closing but operable to open a bypass passageway, the improved continuous catheter flushing devices which utilize rubber outer seal-off sleeves around the capillary inner tubes and squeezably distortable to open a bypass passageway, also are subject to some degree of dampening of the blood pressure pulses and resultant loss of fidelity in the recorded pulse waveforms owing to the yieldability of the rubber sleeves to the blood pressure pulses to which they are subjected in the normal use of the catheter flushing device.

SUMMARY OF THE INVENTION

The present invention contemplates a new and improved flow control device for a continuous catheter flushing system which overcomes all of the above referred to problems and others and provides a device of such type which is of simple and inexpensive lightweight construction composed of a minimum number of quickly and easily assembled component parts, for selectively controlling the flow of flushing solution through the device to either a relatively slow capillary controlled rate or to a relatively fast catheter flushing rate.

Briefly stated, in accordance with one aspect of the invention, a flow control device of the type referred to above is comprised of interfitted body and stem members preferably in the form of molded plastic components, the stem member including a cylindrical drum element projecting into and rotatively engaged in liquid tight relation with the cylindrical wall of a bore chamber in the body member and provided with a diametrical passageway containing a flow restrictor means in the form of a capillary passage for restricting the flow of a liquid medium through the diametrical passageway of the stem member to a capillary controlled relative slow outflow rate when the diametrical passageway is registered with diametrically opposite inlet and outlet port openings in the cylindrical bore wall of the chamber in a spring biased first relative rotative position of the members. The drum element is further provided with an arcuate groove extending circumferentially therearound through an angular extent sufficient to interconnect the diametrically opposite port openings in the chamber bore wall, when the stem and body members are angularly adjusted about their turning axis to a second rotative flow controlling position displaced around 90° or so from the first relative rotative position thereof, to thereby form with the cylindrical wall of the bore chamber a single bypass passageway around the flow restricting diametrical passageway in the stem element, for permitting relatively fast, unrestricted, flow of the liquid medium through the bypass passageway from the inlet port opening in the bore chamber wall out the outlet port opening therein.

In accordance with a further aspect of the invention, the cylindrical drum element of the stem member projects into the bore chamber of the body member from a circular cap end on the stem member forming an annular lip portion on the drum element which abuts against the open rim end of the body member to axially locate the drum element in proper axial position within the bore chamber. The drum element is further provided with a diametrically slotted stud end portion projecting endwise therefrom through a bore opening in an end wall of the body member and snap-locked in place therein to secure the stem and body members together in rotative assembled relation.

In accordance with a still further aspect of the invention, the molded plastic stem and body members are provided with respective actuating arm means extending laterally outward from the members for enabling manual rotation thereof relative to one another between their first and second angularly adjusted flow controlling positions. The actuating arm means on the body member is in the form of a sector-shaped open frame comprised of a pair of side support arms extending radially outward from the body member and interconnected at their outer ends by an arcuate bar portion concentric with the turning axis of the members. The actuating arm means on the stem member is in the form of a single lever arm extending generally radially outward therefrom axially alongside the sector-shaped frame and provided with an axially projecting stop lug extending between and engageable with the side support arms of the open frame to thereby limit the extent of rotative adjustment movement of the members relative to one another to that required to shift them between their first and second angularly adjusted flow controlling positions.

According to yet another aspect of the invention, spring biasing means are provided on the device in energized engagement with the stem and body members thereof to spring bias these members to and normally maintain them in their flow restricting first rotative adjusted position. The spring biasing means suitably comprises a torsion coil spring having a coil portion slip fitted over the cylindrical wall portion of the body member forming the cylindrical bore chamber thereof, and opposite end leg portions extending laterally outward from the coil portion and in spring energized engagement with the respective actuating arm means on the stem and body members so as to spring bias these members to and normally maintain them in their flow restricting first rotative adjusted position.

In accordance with still another aspect of the invention, the cylindrical wall portion of the body member is provided with diametrically opposite, outwardly projecting, in-line tubular connector portions with internal passages communicating with respective ones of the port openings in the cylindrical wall of the bore chamber, the tubular connector portions being provided at their outward ends with fittings for coupling the connector portions to respective tubing sections of, for example, an intravascular catheter tubing system. One of the in-line tubular connector portions serving as the outlet tube of the device is provided with a branch tubular connector portion for connection to diagnostic apparatus for monitoring arterial parameters, the internal passageway of the branch connector portion communicating with the internal passageway of such one in-line tubular connector portion.

The principal object of the invention is to provide a flow control device for a continuous catheter flushing system which is of simple and easily fabricated construction composed of a minimum number of component parts and capable of providing continuous flushing of the catheter with a flushing solution selectively at either a relatively slow capillary controlled flow rate or at a relatively fast flow rate.

Another object of the invention is to provide a flow control device of the above-referred to type and of a construction which assures maximum fidelity of the blood pressure waveforms recorded by pressure transducer apparatus connected to the outlet end of the device.

Still another object of the invention is to provide a flow control device of the above-referred to type which substantially eliminates damping of the blood pressure pulses directed thereinto from the catheter during use.

A further object of the invention is to provide a flow control device of the above-referred to type having a flow restrictor element normally maintained in flow restricting position within the device by a biased valve means which is non-yieldable to blood pressure pulses directed into the device from the catheter during use such as would otherwise cause a damping of the pressure pulses and resulting loss of fidelity in the pressure pulse waveforms produced and/or recorded by pressure monitoring apparatus connected to the outflow end of the flow control device.

A still further object of the invention is to provide a flow control device of the above-referred to type which is light in weight and supportable in suspended position solely by the catheter tubing itself and which may be easily manipulated with only one hand.

Further objects and advantages of the invention will be apparent from the following detailed description of a preferred species thereof and from the accompanying drawings.

BRIEF DESCRIPTION OF THE DRAWINGS

In the drawings:

FIG. 1 is a schematic illustration of a flow control device according to the invention in operative association with a catheter system inserted into the arm of a patient, the device itself being shown on an enlarged scale for purposes of illustration;

FIG. 2 is a perspective view, on an enlarged scale, of the flow control device comprising the invention;

DESCRIPTION OF THE PREFERRED EMBODIMENT

Figure 3:
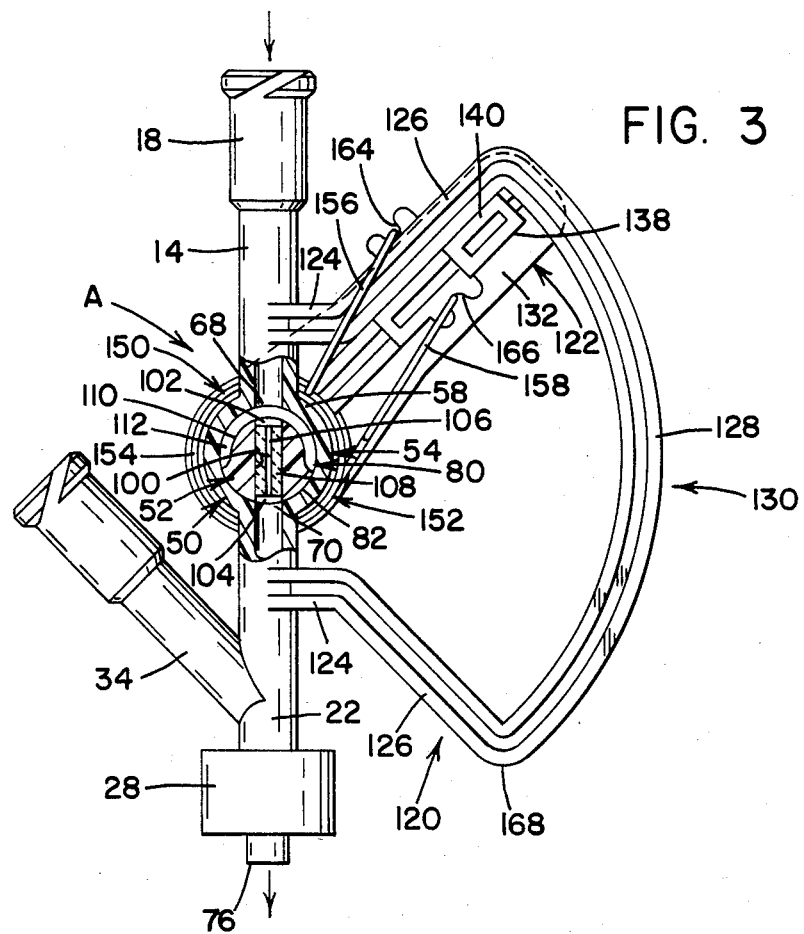
FIG. 3 is a plan view on an enlarged scale, and partly broken away in section, of the flow control device comprising the invention with the body and stem members thereof shown in their flow restricting rotative position.

Referring now to the drawings wherein the showings are for the purposes of illustrating a preferred embodiment of the invention only and not for the purpose of limiting same, the figures show the invention as incorporated, by way of example, into an intravascular catheter system for monitoring arterial pressure and recording of arterial pulse waveforms of a patient as well as for periodically withdrawing blood from or infusing medical fluids into the arterial system of the patient. It is to be understood, however, that the invention may be utilized in various other fluid flow systems, whenever it may be found to have suitable utility therefor.

FIG. 1 illustrates a flow control device A according to the invention incorporated into an intravascular catheter system generally designated 10 and including a tubing section 12 of conventional Tygon tubing, for example, connecting a supply of a medical fluid such as a normal saline solution in a container B to a short tubular inlet connector portion or nipple 14 of the device A by a suitable coupling 16 such as a conventional Luer coupling comprising a male fitting 18 affixed to the free end of the inlet connector tube 14 and releaseably attached to a female fitting 20 affixed to the end of tubing section 12. A short outlet connector tube or nipple 22 of the device A located in-line with the inlet nipple 14 thereof is releaseably attached by a similar coupling 24 to another tubing section 26 of the catheter system 10. Coupling 24 is comprised, as shown, of a female fitting 28 affixed to the free end of the outlet tube 22 and attached to a male fitting 30 affixed to the end of tubing section 26 opposite the catheter end 32 thereof inserted into an artery or vein of an arm of a patient P. The outlet tube 22 is provided with a branch connector tube portion 34 for connection, through a similar coupling 36 and connected tubing section 38, to a conventional monitor or diagnostic apparatus 40, such as a pressure transducer associated with an oscilloscope, for monitoring or recording arterial parameters such as blood pressure, arterial pulse waveforms, stroke volume, heart beat, etc. as mentioned previously.

The catheter 32 used in such vascular catheter systems 10 is very thin, normally having an inside diameter of around $\frac{1}{2}$ millimeters. For the catheter system 10 to operate properly so as to provide accurate monitoring of arterial pressure and recording of pulse waveforms over an extended period of time amounting to several days, the catheter must be maintained open during such time period by preventing the formation of a blood clot or other occlusion at the intravascular end 32 of the catheter inserted into the patient. For this purpose, it has been common practice to continuously pass sufficient infusion or flushing solution through the catheter at a relatively slow rate, but not in such amount as to be harmful to a patient during a relatively long period of monitoring. Thus, depending on the size of the patient, generally from 2 cc to 7 cc per hour of flushing solution passed through the catheter has been found to be safe and to effectively prevent catheter blockage by blood clotting. At the same time, means must be provided for momentarily flushing the catheter from time to time with a rapid flow of the flushing solution through the catheter in order to assure positive clearing out of the catheter of any blood clots or occlusions which have formed or are forming in the catheter, and to also effect rapid clearing of all air from the catheter system and fill or prime the system quickly with the saline infusion solution prior to the insertion of the catheter into an artery or vein of a patient. In addition, a rapid flushing of the catheter is necessary from time to time in order to check the dynamics of the entire catheter system in a manner to avoid inaccuracies in the recorded arterial pressures and pulse waveforms. The flow control device A according to the invention is operable in the catheter system 10 to provide the aforementioned continuous flushing of the catheter 32 with the saline solution from container B normally at the relatively slow flow rate of around 3 cc to 7 cc per hour and selectively from time to time at the mentioned relatively fast flow rate.

As shown in the drawings, the flow control device A comprises, in general, an assembly of two separate molded plastic members, i.e., a body member 50 and a stem member 52 which are adapted to be snap-locked together in assembled relation to each other. Body member 50 is comprised of a cup-shaped housing portion 54 having a flat end wall 56 and a cylindrical side wall portion 58 together defining a bore chamber 60 open at the one end 62 of housing portion 54 which is opposite the end wall 56 thereof. End wall 56 is provided with a centrally located circular bore opening 64 therethrough coaxial with the axis of the cylindrical bore wall surface 66 of bore chamber 60.

Diametrically opposite inlet and outlet port openings 68 and 70, respectively, opening into the chamber 60 are provided in the side wall 58 of the body member 50, at locations thereon more or less mid-way between the end wall 56 and the open outer end 62 of the body member, for the passage into and out of the chamber 60 of a liquid medium, i.e., the saline solution from container B in the particular catheter system 10 illustrated. The body member 50 is provided with inlet and outlet tubular connector portions or nipples 14 and 22, respectively, as referred to previously, which extend radially outward from the cylindrical side wall 58 of the housing portion 54 of the body member in diametrically opposite in-line relation therefrom and in axial alignment with, and their internal passageways 72 and 74 in communication with the respective inlet and outlet port openings 68 and 70 in the chamber wall 58. Affixed to the ends of the in-line tubular connector portions 14 and 22 are the male and female fittings 18 and 28 referred to previously, for attachment to the corresponding female and male fittings 20 and 30 affixed to the tubing sections 12 and 26. The previously mentioned side branch tubular connector portion 34 on the outlet tubular connector portion 22 extends therefrom at a relatively acute angle, e.g., around 45° or so, backwardly from the outer end 76 of such connector portion 22, and its internal passageway 78 communicates with the internal passageway 74 of connector portion 22.

The stem member 52 of the flow control device A is comprised of a cylindrical drum element or portion 80 extending into and rotatively supported in the chamber 60 of the body member 50. Drum element 80 has its cylindrical outer surface 82 rotatively engaged in liquid-tight relation with the cylindrical bore wall surface 66 of chamber 60 so as to rotatively support the stem member on the body member 50 for relative rotative movement about the axis of the bore chamber. The stem member 52 is secured in assembled rotative relation with the body member 50 with the flat inner end 84 of the drum element 80 abutting endwise against the flat inner face 86 of the end wall 56 of the body member 50 and with an outward flange 88 on the outer end of the drum element overlapping and abutting against the outer rim end 62 of the body member.

The drum element 80 of the stem member 52 is provided with a diametrically slotted stud end portion 90 projecting axially of the drum element from the inner end 84 thereof. Stud end portion 90 extends into and through the bore opening 64 in end wall 56 of the body member 50 with a slight clearance therebetween and it is provided with a diametrical slot 92 and a rounded or tapered head end 94 of enlarged size, relative to the cylindrical portion of the stud end, in a direction normal to the slot 92. The provision of the diametrical slot 92 in the stud end portion 90 enables the spring contraction thereof into, and the passage of the stud end portion through the bore opening 64 in the body member 50 so that the enlarged head end 94 will snap-out behind and engage with outer face 96 of the end wall 56 of the body member to thereby snap-lock the stem member 52 in assembled rotative relation with the body member, with the outward flange 88 on the drum element 80 held against the outer rim end 62 of the side wall 58 of body member 50 and with the inner end 84 of the drum element 80 held against the inner face 86 of the end wall 56 of body member 50.

Drum element 80 is provided more or less medially of its ends with a restricted flow bore passageway 100 therethrough which extends diametrically across the drum element with its opposite ends 102, 104 opening at the cylindrical surface 82 of the drum element on diametrically opposite sides thereof. The open ends 102, 104 of the transverse bore passageway 100 are located at points along the length of the drum element 80 to register with the port openings 68 and 70, respectively, in the cylindrical side wall 58 of the body member 50 when the body and stem members 50, 52 are rotatively adjusted to their restricted flow position as shown in FIG. 3.

The bore passageway 100 is provided with suitable flow restriction means for limiting the amount of the flushing solution from container B passing through the bore passageway 100 to a desired relatively slow rate, for example, around 3 cc per hour. The flow restriction means is provided by forming the bore passageway 100 with a capillary section 106 having a very small diameter on the order of several hundredths of a millimeter. As shown, the flow restriction means is preferably provided by positioning a flow resistor element in the form of a marine bore capillary glass tube 108 within the bore passageway 100. The capillary glass tube 108 is formed with the capillary bore passage 106 extending axially thereof and it is force fitted into the bore passageway 100 so as to have a tight leak-proof seal therewith.

The capillary glass tube 108 with its minute capillary bore passage 106 provides a high resistance to flow therethrough of the saline flushing solution from container B. An increase or decrease in the length of the capillary bore passage 106 which may be around one centimeter, for example, will decrease or increase the rate of flow in a linear manner. Also, small variations in the diameter of the capillary bore passage 106 will cause relatively large variations in the amount of fluid flow at a slow rate. Accordingly, the length and diameter of the capillary bore passage 106 is so selected, in relation to the resistances of the catheter and any filters or other flow resistances in the catheter tubing system, and in relation to the pressure of the flushing solution in the pressurized container B, to provide the aforementioned slow rate of flow of about 3 cc per hour for constantly flushing the catheter to avoid the formation of any occlusion therein by blood clotting. Such a relative slow flow rate of the flushing solution will not interfere with or lessen the high quality of the clinical recording of the central arterial pulse waveforms by the intravascular catheter system 10.

Figure 5:
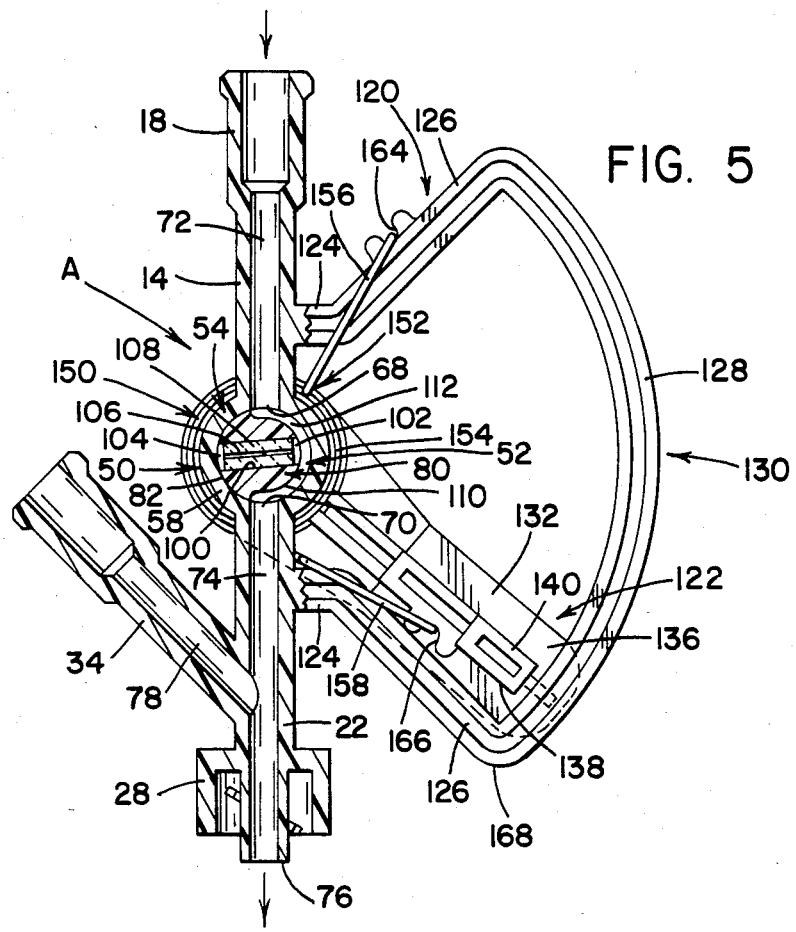
FIG. 5 is a plan view similar to FIG. 3 and partly in section but showing the body and stem members of the device in their fast flow rotative position.
Figure 6:
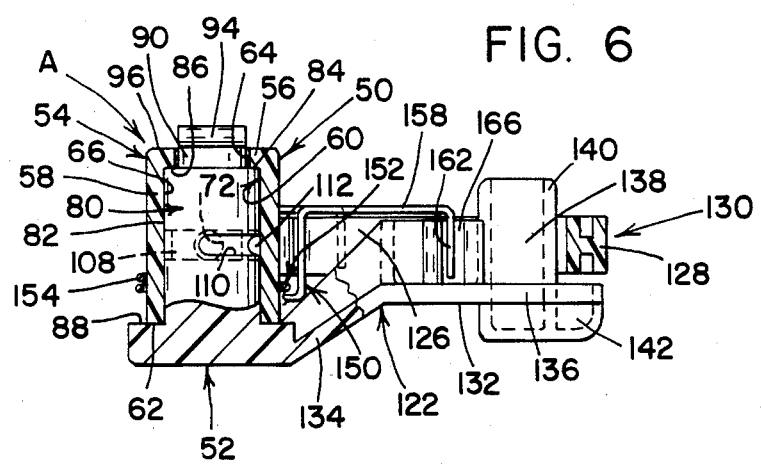
FIG. 6 is an elevation view partly broken away in section, of the device as shown in FIG. 5; and, FIG. 7 is an exploded perspective view of the component members of the device shown in position for assembly.
Figure 7:
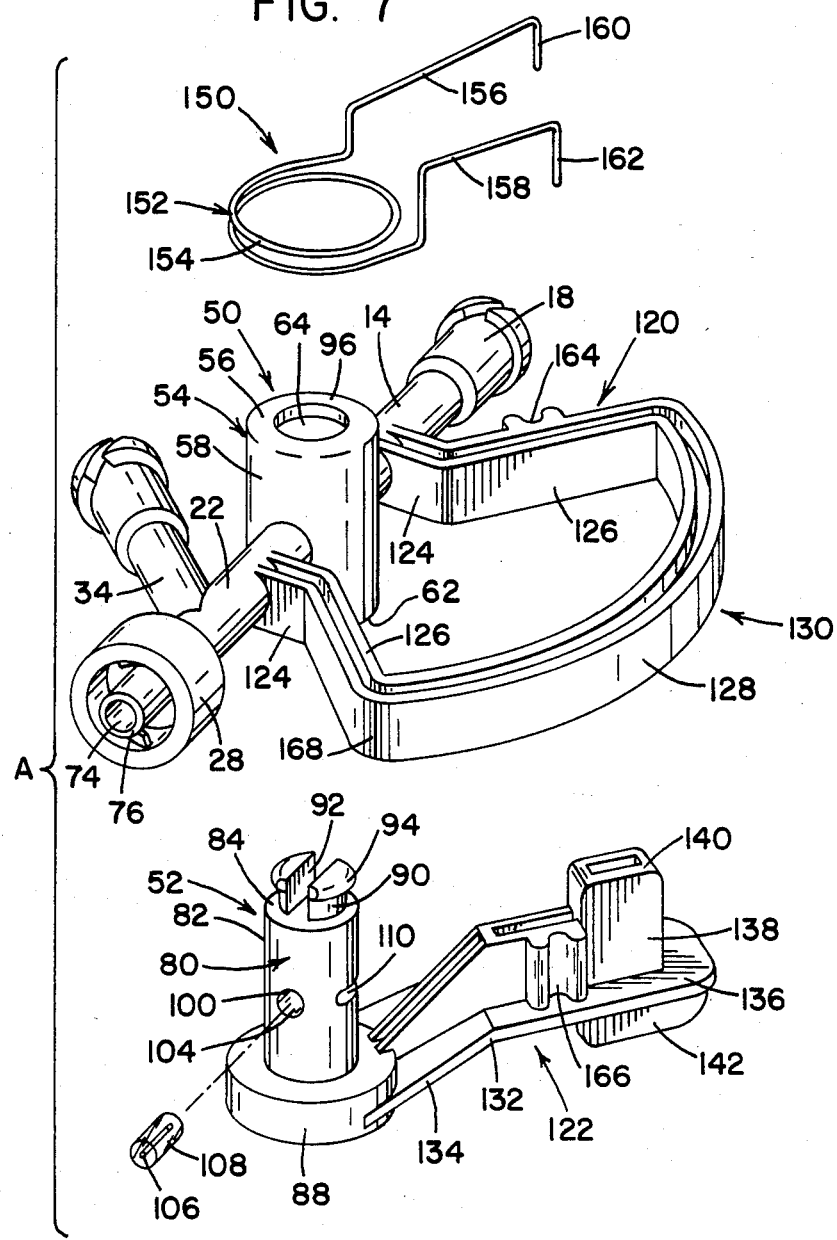

In further accordance with the invention, the drum element 80 is provided with an arcuate groove 110 in the cylindrical outer surface 82 thereof extending more or less equidistantly to each side of the diametrical bore passageway and located at a point axially of drum element 80 corresponding to the diametrical bore passageway 100 therein and to the port openings 68, 70 in the side wall 58 of the body member 50 so as to open into, and communicate at its opposite ends with the port openings when the body and stem members 50, 52 are rotatively moved to their fast flow relative rotative position as shown in FIGS. 5 and 6. The arcuate groove 110 thus forms, together with the cylindrical bore wall surface 66 of bore chamber 80, a bypass passageway 112 which extends around the restricted flow passageway 100 and interconnects the port openings 68, 70 to permit unrestricted, relatively fast full flow of the catheter flushing solution into the catheter tube 26 and tip 32 when the body and stem members 50, 52 are rotatively adjusted to their fast flow relative position, shown in FIGS. 5 and 6, rotatively spaced approximately 90° or so from their restricted flow relative rotative position shown in FIG. 3.

The body and stem members 50, 52 are provided with respective actuating arm means 120, 122 for enabling convenient manual rotative adjustment of the members relative to one another from their normal restricted, or slow flow rate, relative rotative position to their unrestricted, or fast flow rate, relative rotative position. The actuating arm means 120 on the body member 50 comprises a pair of support arms 124 extending in the same direction laterally outward from the respective tubular connector portions 14, 22 in an axial plane thereof normal to the turning axis of the members 50, 52, and to that side of the connector portions 14, 22 opposite the sides on which the branch connector tube 34 extends from tubular connector portion 22. The support arms 124 have outer end portions 126 extending generally radially of the turning axis of the body and stem members 50, 52 in diverging relation to each other and interconnected at their outermost ends by an arcuate bar portion 128 concentric with the turning axis of members 50, 52 and forming, with the diverging outer end portions 126 of the support arms 124, a sector-shaped open frame 130 extending outwardly from the body member 50 in a plane which is normal to the turning axis of the body and stem members 50, 52 and which includes the in-line axes of the tubular connector portions 14, 22.

Figure 4:
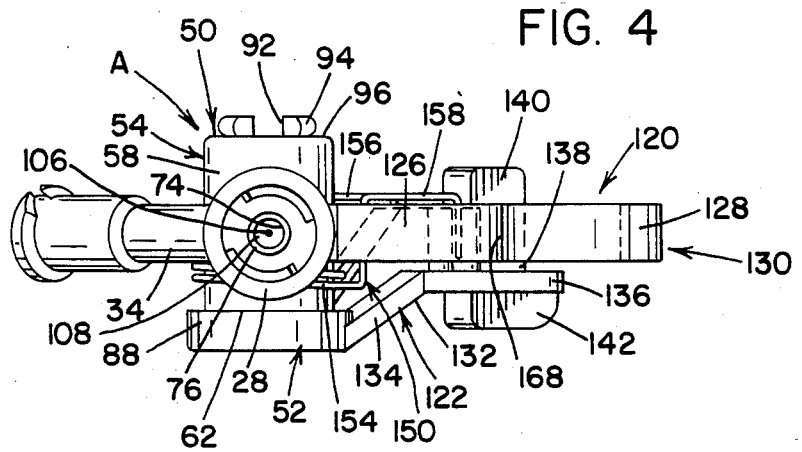
FIG. 4 is an elevation view on an enlarged scale of the flow control device shown in FIG. 3.

The actuating arm means 122 on the stem member 52 comprises a single lever arm 132 extending generally radially outward from the outward flange portion 88 of the stem member 52 and angularly located therearound so as to swing in an arc defined by the diverging support arm portions 126 of the sector-shaped frame 130, when the body and stem members 50, 52 are rotatively moved relative to one another from their normal restrictive flow first relative rotative position to their unrestricted fast flow or second relative rotative position. As shown best in FIGS. 4 and 6, the single lever 132 is axially offset intermediate the ends thereof, as indicated at 134, in a direction toward the sector-shaped open frame 130 of the actuating arm means 120 on the body member 50, so as to locate the outer end portion 136 of the lever arm 132 in a position axially alongside the sector-shaped frame 130. The lever arm 132 is provided with a projection 138 extending from its outer end portion 136 in a direction axially of the drum element 80 of stem member 52 and through the space defined by the sector-shaped open frame 130 on the body member 50. The projection 138 forms a stop member which is engageable with the outer end portions 126 of support arms 124 of the sector-shaped frame 130 to limit the extent of rotative movement of the body and stem members 50, 52 relative to one another to the angular degree required to shift them between their normal restricted flow relative rotative position and their unrestricted or fast flow relative rotative position. The stop member 138 projects beyond the plane of the frame 130, as shown at 140, to thereby serve as a finger engageable lug for manually swinging the lever arm 132 so as to rotate the stem member 52 relative to body member 50. A similar projection 142 on the opposite side of lever arm 132 from projection 140 serves as a further finger engageable lug located to the opposite side of the frame 130 for manually actuating the lever arm 132.

For the proper operation of the flow control device A according to the invention, it is necessary for the body and stem members 50, 52 to be biased to and normally maintained in their restricted or slow flow rotative position relative to one another. For this purpose, suitable biasing spring means 150 are provided on the device for yieldably holding the members 50, 52 in their restricted or slow flow rate position, as shown in FIG. 3. As there shown, the biasing spring means 150 preferably comprises a torsion coil spring 152 having a helical portion 154 slip fitted onto the open end portion of the cylindrical side wall 58 of the housing portion 54 of body member 50 so as to be retained in place thereon between the lever arm 132 and the pair of support arms 124, and laterally outward projecting, axially offset, thrust end leg portions 156 and 158 with axially extending bent contact end legs 160 and 162, respectively, caught in and spring held in respective notches 164 and 166 formed in the sides of one of the support arm portions 126 and in the lever arm 132 to retain the contact end legs 160, 162 in proper spring pressed engagement in notches 164, 166 with the one support arm 124 and the lever arm 132 at all times. The helical coil portion 154 of the torsion coil spring 152 is, of course, wound in a direction such that the torsional force thereof normally urges the end legs 156, 158 of the spring toward one another so as to normally hold the end leg 158 in the position shown in FIG. 3, with its stop member 138 engaged with the one support arm portion 126, thereby maintaining the body and stem members 50, 52 in their normal, restricted flow rate rotative position relative to one another.

It will be apparent that any other suitable form of biasing spring means 150 than the illustrated torsion coil spring 152 may be employed such as, for example, a tension coil spring connected at its opposite ends in a tensioned condition between the lever arm 132 and the outer end portion 126 of the one support arm 124; or a compression coil spring may be compressed between the lever arm 132 and the outer end portion 126 of the other one support arm 124.

In assembling the flow control device A comprising the invention, the torsion coil spring 152 is first mounted in place on the body member 50 by slipping the helical coil portion 154 of the spring over the open end of the cylindrical housing portion 54 of the body member 50, and then flexibly distorting the thrust end leg 156 and its contact and leg 160 into the notch 164 in the outer end portion 126 of the one support arm 124 of frame 130. The stem member 52, with the capillary glass tube 108 inserted in place in the diametrical passageway 100 of drum element 80, is then assembled with the body member 50 by inserting the drum element thereof into the bore chamber 60 to snap-lock the members 50, 52 together, as described previously, while at the same time torsionally springing the thrust end leg 158 of the torsion coil spring 152 away from the other thrust end leg 156 in order to permit the passage of the lever arm 132 of stem member 52 into position between the flexed end leg 158 and the adjacent support arm 124 of the sector-shaped frame 130 for engagement of the bent contact end 162 of the end leg 158 in the notch 166 on the lever arm 132, thereby completing the assembly of the device A.

In its use in an intravascular catheter system 10 as described hereinabove, the flow device A comprising the invention is efficient and reliable in operation, and does not produce any damping of blood pressure pulses such as would cause inaccuracies and loss of fidelity in the recorded pressure pulses and waveforms. In addition, the flow device A is of light weight so as to be easily suspended and supported in place solely by the light weight pliable plastic tubing sections 12 and 26 of the catheter system 10, and it is easily manipulated, the finger engageable projections 140 or 142 on the normally spring held lever arm 132 being located within easy one-hand grippable reach of the far end 168 of the sector-shape frame 130 to enable the easy rotative swing movement of the body and stem members 50, 52 to their unrestricted fast flow relative rotative position by a squeezing force applied thereto between the fingers and thumb of an operator's one hand.

Prior to the insertion of the catheter tip 32 of the catheter system 10 into an artery or vein of a patient P, the flow control device A according to the invention is, as shown, connected between the catheter 26 and the source of saline flushing solution in the container B which is either pressurized, or elevated sufficiently above the patient, so as to provide the necessary working upstream pressure for proper flow of the flushing solution from the container through the flow restricting bore passageway 100 of the device A. As previously described, this passageway 100 is normally maintained in its flow restricting position shown in FIG. 3 by the torsional force of the biasing spring means 150 acting to normally maintain the body and stem members 50, 52 in their flow restricting rotative position relative to one another. All air bubbles are first eliminated from the catheter system 10 by momentarily actuating the lever arm 132 relative to the frame 130 so as to rotatively shift the body and stem members 50, 52 to their unrestricted or fast flow flushing position relative to one another, as shown in FIG. 5. In this position, the bypass passageway 112 around the restricted flow passageway 100 then interconnects the port openings 68, 70 in the body member housing 54 to establish a fast flow of the flushing solution through the device A and through the catheter 26 and catheter tip 32 such as effectively eliminates any air bubbles in the catheter system and removes any occlusions therein as well as priming the catheter system with the flushing solution in readiness for insertion of the catheter into the patient's artery or vein.

When all air bubbles have been eliminated from the catheter system 10, the squeezing action on the lever arm 132 and sector-shaped frame 130 is terminated, thereby freeing the body and stem members 50, 52 for return rotative movement to their normal restricted flow position, as shown in FIG. 3, by the spring force of the biasing spring means 150, with only the limited flow of flushing solution through the passageway 100 containing the capillary passage 106 then continuing. The catheter tip 32 is then inserted into the artery or vein of the patient P, with only the relatively slow flow of catheter flushing solution then passing through the device A and catheter 26 being injected into the artery or vein of the patient. This continuous flow of flushing solution through the catheter reduces the likelihood of development of blood clots or other occlusions in the tip end 32 of the catheter positioned in the patient's artery or vein.

The branch connector tube 34 of the catheter system 10 is connected to whatever monitoring or recording system is desired, or to a pressure transducer for oscilloscope observations. To assure high quality of the information provided by the catheter system and monitoring means, the system is momentarily flushed from time to time with a relatively rapid flow of the flushing flow by manually actuating the lever arm 132 relative to the sector-shaped frame 130 for a short instant or so in order to permit the flushing solution from container B to rapidly flow around or bypass the restricted flow passageways 100, 106 of the device A and pass into and through the catheter 26 for the purpose of clearing the inserted catheter tip 32 of any blood clots or other occlusions that may have formed therein in the meantime, and otherwise checking the dynamics of the catheter system. When the manual actuation of the lever arm 132 and sector-shaped frame 130 is terminated, the relatively rapid flow of the flushing solution through the device A and catheter 26 stops, and the restricted normal slow flow of the flushing solution through the device A and the catheter 26 is then reinstituted and continues once again. The periodic fast flushing of the catheter 26 as thus described is accomplished quickly and easily by the use of only one hand of the person operating the device A.

Because of the absence in the flow control device A according to the invention and associated catheter 26 of any yieldable element which is exposed to and thus would yield at least to some degree to the blood pressure pulses transmitted to the device back through the flushing solution continuously filling the catheter and the device, there is therefore no damping of these pressure pulses within the device A such as would result in inaccurate recordings or indications of the patient's actual pressure pulses and waveforms by the monitoring or diagnostic recording apparatus 40. As a result, catheter systems 10 equipped with the catheter flushing flow control device A comprising the invention provide appreciably more accurate and truer recordings of a patient's actual blood pressure pulses and waveforms than prior art flow control devices used in intravenous catheter systems such as, for example, those devices provided with squeezable rubber sleeve valves around the glass capillary flow restrictor tubes which sleeves are exposed to and thus yield to and damp the actual pressure pulses so that the recordings and indications of these pressure pulses and waveforms by the associated monitoring equipment is inaccurate and lacking in fidelity.

Having thus described the invention, it is claimed:

1. A continuous catheter flushing flow control device comprising a body member having a cylindrical bore chamber and provided with a pair of diametrically opposite port openings in the cylindrical wall of said bore chamber, a stem member comprising a cylindrical drum element extending into and rotatively engaged in liquid tight relation with the cylindrical bore wall of said chamber, interengaging means on said body and stem members locking said drum element axially within the said chamber without hindering rotative movement of the stem member therewithin, said drum element having a diametrical passageway extending transversely therethrough for registering with and interconnecting said port openings in a first relative rotative flow controlling position of said members, flow restrictor means in said passageway comprising a capillary passage therein for restricting the flow of liquid through said passageway to a relatively slow capillary controlled rate, said drum element further having an arcuate groove extending circumferentially therearound through an angular extent sufficient to interconnect the said port openings, when the said members are relatively rotated to a second rotative flow controlling position angularly displaced around 90° from the said first relative rotative position thereof, to thereby form with the cylindrical wall of said bore chamber a single bypass passageway around the said diametrical passageway and the flow restrictor means therein, said arcuate groove and bypass passageway having a cross-sectional size throughout sufficient to permit a relatively large unrestricted flow of liquid through said bypass passageway from one to the other of said port openings, said members being biased so as to be normally held in their said flow restricting first relative rotative position.

2. A device as defined in claim 1, wherein the said flow restrictor means comprises a marine bore glass capillary tube inserted in said diametrical passageway in liquid tight relation with the wall thereof.

3. A device as defined in claim 1, wherein the said body member is provided with diametrically opposite outwardly projecting in-line tubular connector portions with internal passages therethrough communicating with respective ones of the said port openings in the said cylindrical wall of said bore chamber, said tubular connector portions being provided at their outward ends with fittings for coupling said connector portions to respective tubing sections of a catheter tubing system.

4. A device as defined in claim 1, wherein the said body and stem members are provided with respective actuating arm means extending laterally outward from the said members for manual rotation thereof relative to one another about their turning axis.

5. A device as defined in claim 4, wherein the said actuating arm means are located within conjoint one hand grippable reach of each other throughout the full angular extent of relative rotative movement of said members between their said first and second flow controlling positions.

6. A device as defined in claim 1, wherein spring means are provided on said device in energized spring-biasing engagement with said members to normally hold them in their said flow restricting first relative rotative position.

7. A device as defined in claim 4, wherein external spring means are provided on said device in energized engagement with the said actuating arm means so as to spring bias said members to and normally hold them in their said flow restricting first relative rotative position.

8. A device as defined in claim 6, wherein the said spring means comprises a torsion coil spring having a coil portion slip fitted over the said cylindrical wall of said body member and opposite end portions of said coil portion in spring energized engagement with said members to normally hold them in their said flow restricting first relative rotative position.

9. A device as defined in claim 7, wherein the said spring means comprises a torsion coil spring having a coil portion slip fitted over the said cylindrical wall of said body member and opposite end leg portions extending laterally outward from said coil portion and in spring energized engagement with the said actuating arm means so as to spring bias said members to and normally hold them in their said flow restricting first relative rotative position.

10. A device as defined in claim 4, wherein the said actuating arm means on one of said members comprises a pair of support arms extending laterally outward therefrom and having outer end portions extending generally radially of the said cylindrical wall of said bore chamber and interconnected at their outermost ends by an arcuate bar portion concentric with the turning axis of said members and forming with said support arm outer end portions a sector-shaped open frame on said one member, and the said actuating arm means on the other one of said members comprises a single lever arm extending generally radially outward from said other one member and axially alongside the said sector-shaped frame, said lever arm having a projection extending between and engageable with the said support arms to limit the extent of rotative movement of said members relative to one another to that required to shift them between their said first and second flow controlling positions.

11. A device as defined in claim 10, wherein the said support arms extend laterally outward from, and the said frame is supported on said body member, and the said single lever arm extends radially outward from the said stem member.

12. A device as defined in claim 11, wherein the said body member is provided with diametrically opposite outwardly projecting in-line tubular connector portions with internal passages therethrough communicating with respective ones of the said port openings in the said cylindrical wall of said bore chamber, said tubular connector portions being provided at their outward ends with fittings for coupling said connector portions to respective tubing sections of a catheter tubing system, and the said support arms of said sector-shaped frame extending laterally outward from the said tubular connector portions on said body member.

13. A device as defined in claim 3, wherein one of said in-line tubular connector portions is provided with a branch tubular connector portion having an internal passageway communicating with the internal passageway of the said one connector portion for connection to diagnostic apparatus for monitoring arterial parameters.

14. A continuous catheter flushing flow control device comprising a cup-shaped body member having an end wall and a surrounding cylindrical side wall defining therewith a cylindrical bore chamber open at the end opposite said end wall, said side wall being provided with a pair of diametrically opposite port openings therein opening into said chamber, a stem member comprising a cylindrical drum element extending into the said open end of and rotatively engaged in liquid tight relation with the cylindrical bore wall of said chamber, a stud end portion projecting endwise from said drum element through a bore opening in said end wall and snap-locked in place therein to secure the said members together in rotative assembled relation, said drum element having a diametrical passageway extending transversely therethrough for registering with and interconnecting said port openings in a first relative rotative flow controlling position of said members, flow restrictor means in said passageway comprising a capillary passage therein for restricting the flow of liquid through said passageway to a relatively slow capillary controlled rate, said drum element further having an arcuate groove extending circumferentially therearound through an angular extent sufficient to interconnect the said port openings, when the said members are relatively rotated to a second rotative flow controlling position angularly displaced around 90° from the said first relative rotative position thereof, to thereby form with the cylindrical wall of said bore chamber a single bypass passageway around the said diametrical passageway and the flow restrictor means therein, said arcuate groove and bypass passageway having a crosssectional size throughout sufficient to permit a relatively large unrestricted flow of liquid through said bypass passageway from one to the other of said port openings, said members being biased so as to be normally held in their said flow restricting first relative rotative position.

15. A device as defined in claim 14, wherein the said flow restrictor means comprises a marine bore capillary tube inserted in said diametrical passageway in liquid tight relation with the wall thereof.

16. A device as defined in claim 14, wherein the said arcuate groove extends around the said drum element through an angle slightly greater than 180° and approximately equidistant to each side of one end of the said diametrical passageway in said drum element.

17. A device as defined in claim 14, wherein the said projecting stud end portion of said drum element is diametrically slotted to permit the spring contraction thereof to a smaller diametrical dimension across one of its diameters for insertion through a bore opening in said end wall, and said projecting stud end portion is provided around its outermost end with laterally outward extending locking lip means of cam-shaped section for engaging with the wall of said bore opening to contract the said slotted stud end portion for insertion into and passage through said bore opening to snap-lock behind said end wall.

18. A device as defined in claim 17, wherein the said arcuate groove extends around the said drum element through an angle slightly greater than 180° and approximately equidistant to each side of one end of the said diametrical passageway in said drum element.

19. A device as defined in claim 14, wherein the said body member is provided with diametrically opposite outwardly projecting in-line tubular connector portions with internal passages therethrough communicating with respective ones of the said port openings in the said side wall of said body member, said tubular connector portions being provided at their outward ends with fittings for coupling said connector portions to respective tubing sections of a catheter tubing system.

20. A device as defined in claim 14, wherein the said body and stem members are provided with respective actuating arm means extending laterally outward from the said members for manual rotation thereof relative to one another about their turning axis.

21. A device as defined in claim 17, wherein the said body and stem members are provided with respective actuating arm means extending laterally outward from the said members for manual rotation thereof relative to one another about their turning axis.

22. A device as defined in claim 14, wherein spring means are provided on said device in energized spring biasing engagement with said members to normally hold them in their said flow restricting first relative rotative position.

23. A device as defined in claim 20, wherein external spring means are provided on said device in energized engagement with the said actuating arm means so as to spring bias said members to and normally hold them in their said flow restricting first relative rotative position.

24. A device as defined in claim 22, wherein the said spring means comprises a torsion coil spring having a coil portion slip fitted over the said cylindrical side wall of said body member and opposite end portions of said coil portion in spring energized engagement with said members to normally hold them in their said flow restricting first relative rotative position.

25. A device as defined in claim 23, wherein the said spring means comprises a torsion coil spring having a coil portion slip fitted over the said cylindrical side wall of said body member and opposite end leg portions of said coil portion in spring energized engagement with the said actuating arm means so as to spring bias said members to and normally hold them in their said flow restricting first relative rotative position.

26. A device as defined in claim 17, wherein spring means are provided on said device in energized spring biasing engagement with said members to normally hold them in their said flow restricting first relative rotative position.

27. A device as defined in claim 21, wherein external spring means are provided on said device in energized engagement with the said actuating arm means so as to spring bias said members to and normally hold them in their said flow restricting first relative rotative position.

28. A device as defined in claim 26, wherein the said spring means comprises a torsion coil spring having a coil portion slip fitted over the said cylindrical side wall of said body member and opposite end portions of said coil portion in spring energized engagement with said members to normally hold them in their said flow restricting first relative rotative position.

29. A device as defined in claim 27, wherein the said spring means comprises a torsion coil spring having a coil portion slip fitted over the said cylindrical side wall of said body member and opposite end leg portions of said coil portion in spring energized engagement with the said actuating arm means so as to spring bias said members to and normally hold them in their said flow restricting first relative rotative position.

30. A device as defined in claim 20, wherein the said actuating arm means on one of said members comprises a pair of support arms extending laterally outward from said one member and having outer end portions extending generally radially of the turning axis of said members and interconnected at their outermost ends by an arcuate bar portion concentric with the turning axis of said members and forming with said support arm outer end portions a sector-shaped open frame on said one member, and the said actuating arm means on the other one of said members comprises a single lever arm extending generally radially outward from said other one member and axially alongside the said sector-shaped frame, said lever arm having a projection extending between said support arms through the space defined by said frame and engageable with the said support arms to limit the extent of rotative movement of said members relative to one another to that required to shift them between their said first and second flow controlling positions.

31. A device as defined in claim 30, wherein the said support arms extend laterally outward from, and the said frame is supported on said body member, and the said single lever arm extends radially outward from the said stem member.

* * * * *